US005482047A

United States Patent [19]
Nordgren et al.

[11] Patent Number: 5,482,047
[45] Date of Patent: Jan. 9, 1996

[54] INTRAOPERATIVE ULTRASOUND PROBE

[75] Inventors: Timothy F. Nordgren, Bothell; Deborah K. Imling, Bellevue; Joseph L. Ungari, Everett; Donald G. Killam; Ronald E. McKeighen, both of Woodinville, all of Wash.

[73] Assignee: Advanced Technology Laboratories, Inc., Bothell, Wash.

[21] Appl. No.: 349,593

[22] Filed: Dec. 5, 1994

Related U.S. Application Data

[62] Division of Ser. No. 155,447, Nov. 19, 1993, Pat. No. 5,381,795.

[30] Foreign Application Priority Data

Nov. 23, 1992 [GB] United Kingdom ............... 9224585

[51] Int. Cl.⁶ ................................................. A61B 8/00
[52] U.S. Cl. ..................... 128/662.03; 29/884; 174/263; 439/50; 439/74
[58] Field of Search ............... 128/660.09, 660.10, 128/661.01, 662.03; 439/44, 49, 50, 52, 53, 63, 74; 174/261, 262, 263; 29/760, 834, 842, 884

[56] References Cited

U.S. PATENT DOCUMENTS

| | | |
|---|---|---|
| 3,069,753 | 12/1962 | Lalmond et al. . |
| 3,509,513 | 4/1970 | Russin . |
| 3,573,719 | 5/1971 | Lightner . |
| 3,605,060 | 9/1971 | Praeger . |
| 3,689,865 | 9/1972 | Pierini et al. . |
| 3,891,013 | 6/1975 | Folk et al. . |
| 3,952,387 | 4/1976 | Iinuma et al. . |
| 4,052,778 | 10/1977 | Siden et al. . |
| 4,060,887 | 12/1977 | DeGroef . |
| 4,076,365 | 2/1978 | Ross et al. . |
| 4,085,502 | 4/1978 | Ostman et al. . |
| 4,178,678 | 12/1979 | Carrillo et al. . |
| 4,273,407 | 6/1981 | Snuffer et al. . |
| 4,313,444 | 2/1982 | Glenn ................................ 128/660.09 |
| 4,365,856 | 12/1982 | Yaegashi et al. . |
| 4,385,255 | 5/1983 | Yamaguchi et al. . |
| 4,476,628 | 10/1984 | Kees, Jr. . |
| 4,668,581 | 5/1987 | Luc et al. . |
| 4,697,339 | 10/1987 | Verhoeven . |
| 4,701,659 | 10/1987 | Fujii et al. . |
| 4,734,046 | 3/1988 | McAllister et al. . |
| 4,763,410 | 8/1988 | Schwartzman . |
| 4,773,140 | 9/1988 | McAusland . |
| 4,815,207 | 3/1989 | Schwartzman . |
| 4,852,249 | 8/1989 | Muskulus et al. . |
| 4,898,177 | 2/1990 | Takano et al. ..................... 128/662.03 |

(List continued on next page.)

FOREIGN PATENT DOCUMENTS

| | | |
|---|---|---|
| 53-5789 | 1/1978 | Japan . |
| 60-202966 | 10/1985 | Japan . |
| 3-48490 | 3/1991 | Japan . |

*Primary Examiner*—George Manuel
*Attorney, Agent, or Firm*—W. Brinton Yorks, Jr.

[57] ABSTRACT

An intraoperative ultrasonic transducer probe is described comprising a handle section and a transducer section which resemble a tiny leg and foot. The two sections are obtusely angled relative to each other so that the physician may continue to clearly view the surgical site while holding and manipulating the probe. The extension of the transducer section away from its point of attachment to the handle section results in the toe of the foot being insertable under unincised tissue, enabling the surgeon to ultrasonically examine organs and tissue peripheral to the surgical site and to follow a vessel even beyond the incision. The transducer section is completely encapsulated in a rubberlike material which electrically insulates the transducer from the patient, enables the probe to be easily sterilized, and further provides an inherent standoff between the transducer and the contact surface of the probe. Thus, the transducer can be focused immediately at the skin line of the organ or vessel which is in contact with the probe. The probe can be easily assembled by providing termination assemblies for attaching coaxial cable conductors to the printed circuit board assembly of the probe.

11 Claims, 7 Drawing Sheets

U.S. PATENT DOCUMENTS

| | | |
|---|---|---|
| 4,929,195 | 5/1990 | Seidoh . |
| 4,993,968 | 2/1991 | Guletsky et al. . |
| 5,010,642 | 4/1991 | Takahashi et al. . |
| 5,016,347 | 5/1991 | Okazaki et al. . |
| 5,120,258 | 6/1992 | Carlton . |
| 5,125,150 | 6/1992 | Meyer . |
| 5,275,167 | 1/1994 | Killam . |
| 5,347,711 | 9/1994 | Wheatcraft et al. . |
| 5,351,691 | 10/1994 | Brommersma ............... 128/662.03 |
| 5,387,764 | 2/1995 | Blom et al. . |

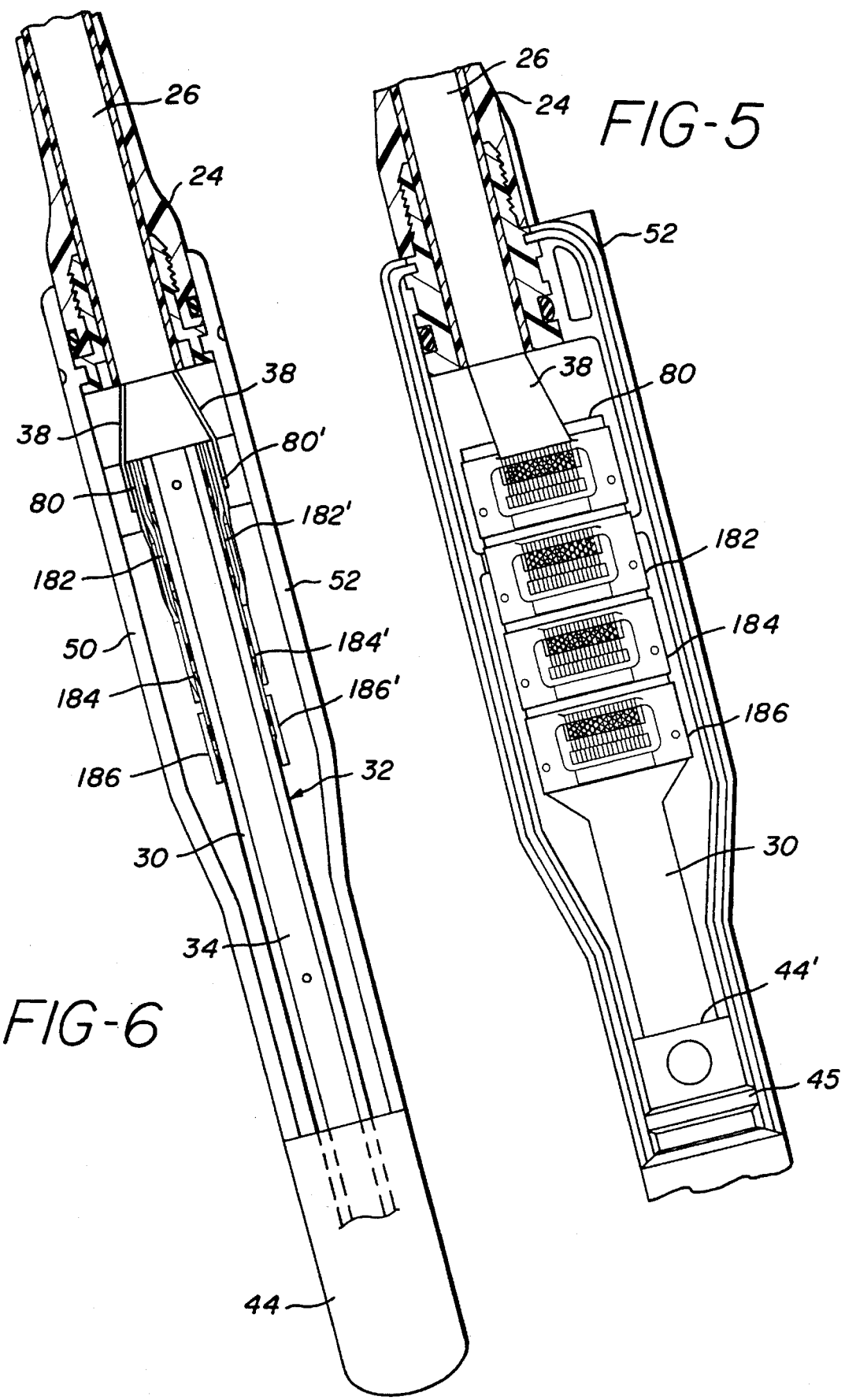

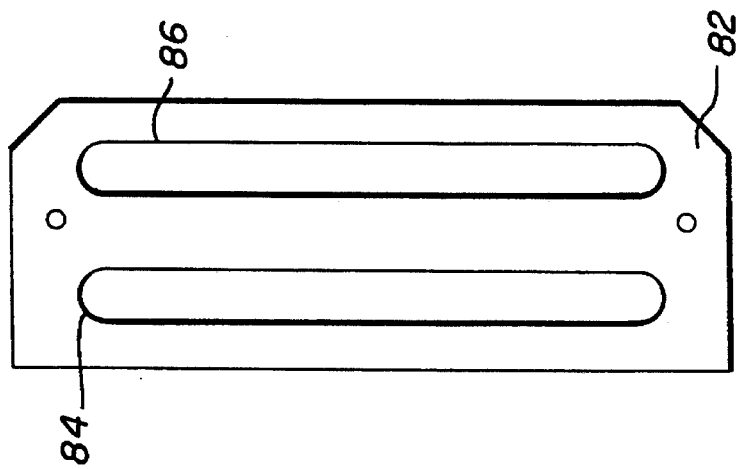
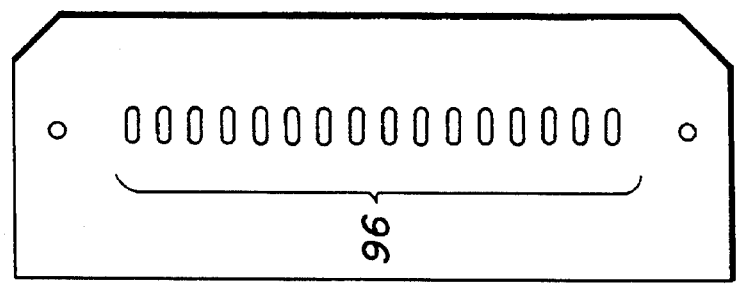
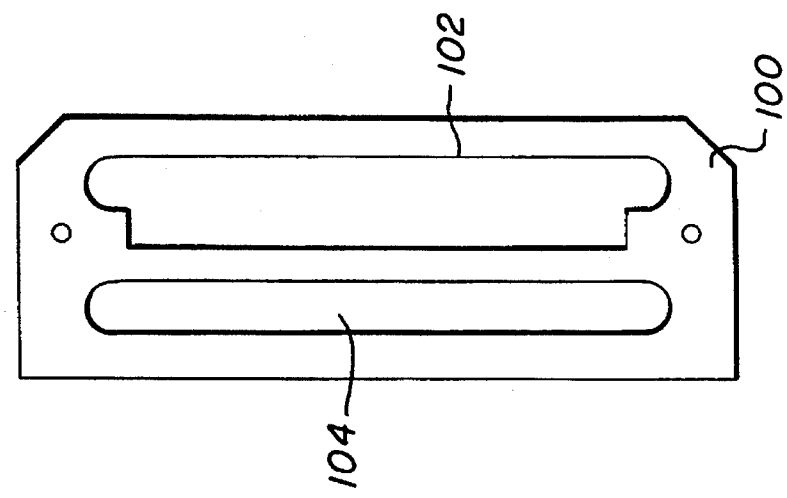

5,482,047

INTRAOPERATIVE ULTRASOUND PROBE

This application is a division of application Ser. No. 08/155447, filed Nov. 19, 1993, and now U.S. Pat. No. 5,381,795.

This invention relates to ultrasonic diagnostic probes or scanheads and, in particular, to ultrasound probes which are uniquely suited for imaging and diagnosing organs of the body and arterial vessels during surgery.

Ultrasonic diagnostic imaging probes, which generally find application during noninvasive procedures, can also be used during surgical procedures. One such procedure where ultrasonic imaging probes have particular utility is during vascular surgery. During vascular surgery, ultrasonic imaging probes can be utilized to image and diagnose the interior of carotid arteries. Another procedure where ultrasonic imaging probes have utility is during transplant surgery where, for example, the ultrasonic imaging probe can be used to verify successful attachment and function of renal arteries.

Surgical ultrasound probes are preferably small and as easily to manipulate as surgical instruments. Such probes should be capable of imaging the blood flow of a vessel which is in immediate contact with the probe. This necessitates focal properties of the probe which enable it to produce a focused image of tissue and structure which is in immediate contact with the probe. Reliability is enhanced by the provision of an all electronic probe with no mechanically moving parts. When using surgical probes it is important that the hand of the physician not obscure the surgical site being examined. Such probes must be adapted for use in a sterile surgical field, must pose no electrical hazard to the patient, and must be easy to clean and sterilize, e.g., should be smoothly and securely integrated and closed with no gaps or openings. Furthermore, such probes should be capable of use around organs and under skin which has not been incised during the surgical procedure.

In accordance with the principles of the present invention an ultrasonic imaging probe is provided for surgical applications. The probe comprises a transducer at its distal end to which is attached a handle for holding the probe. The handle is attached to the transducer end of the probe at a point which is offset from the center of the probe and the handle is angled at an oblique angle relative to the major axis of the transducer end. The piezoelectric transducer of the transducer end of the probe is an electronically steered and focused multi-element transducer with no moving parts. The transducer end of the probe is contained within an encapsulating boot and lens material, which provides reliable electronic insulating properties and is easy to clean and sterilize. The encapsulating boot also performs the function of a standoff, with the multielement transducer being capable of focusing at the tissue which is in immediate contact with the boot. The angulation of the handle permits the physician to grasp and manipulate the probe without blocking the physician's view of the surgical site. The offset attachment of the transducer end and shaft of the probe enables the physician to insert the distal tip of the transducer end under skin which has not been incised to examine tissues and arterial vessels peripheral to the point of incision.

Figure 4:
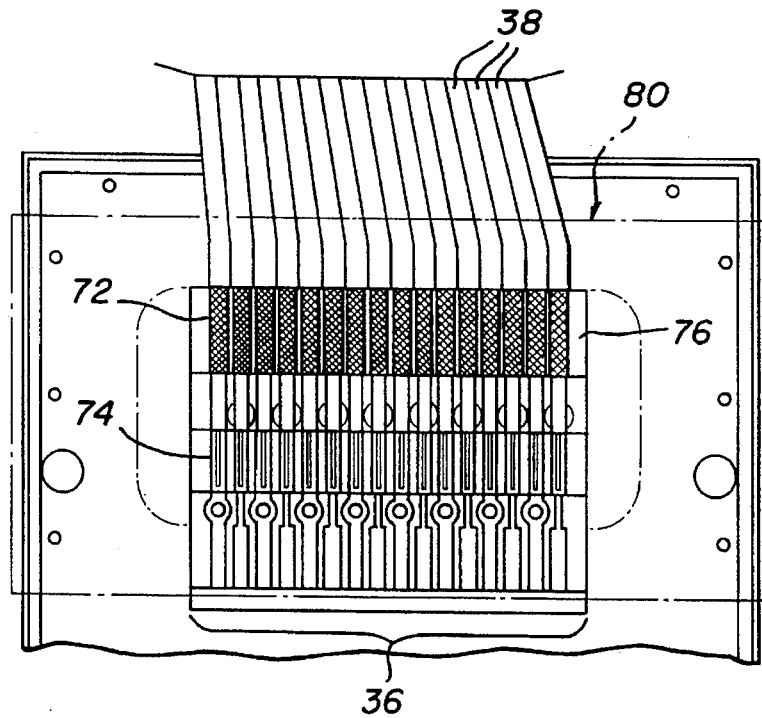
Figure 8:
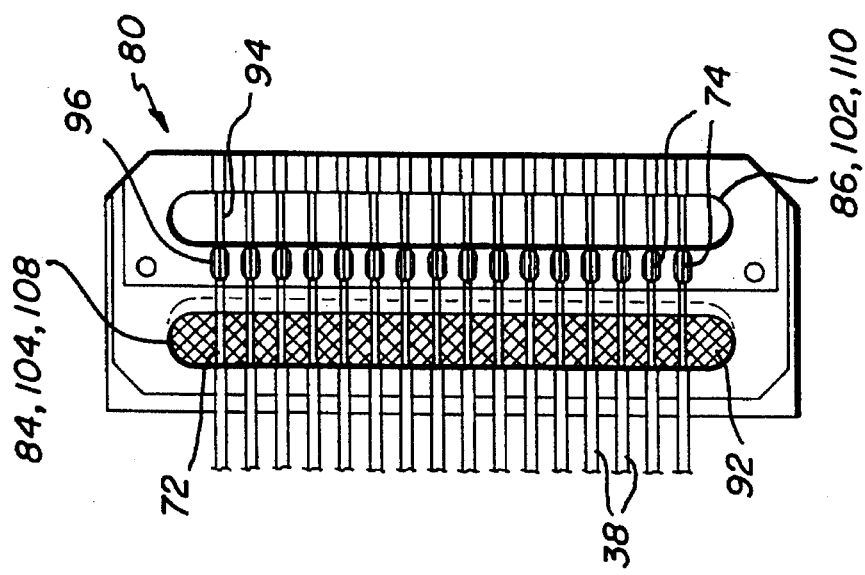

FIG. 4, 5, and 6 illustrate the manner in which the cable is attached to an intraoperative ultrasound probe of the present invention;

FIGS. 7a–7e illustrate the construction of a preferred termination assembly for connecting a multifilament coaxial cable to the intraoperative ultrasound probe of the present invention; and FIG. 8 illustrates the fully assembled termination assembly of FIGS. 7a–7e.

Figure 1:
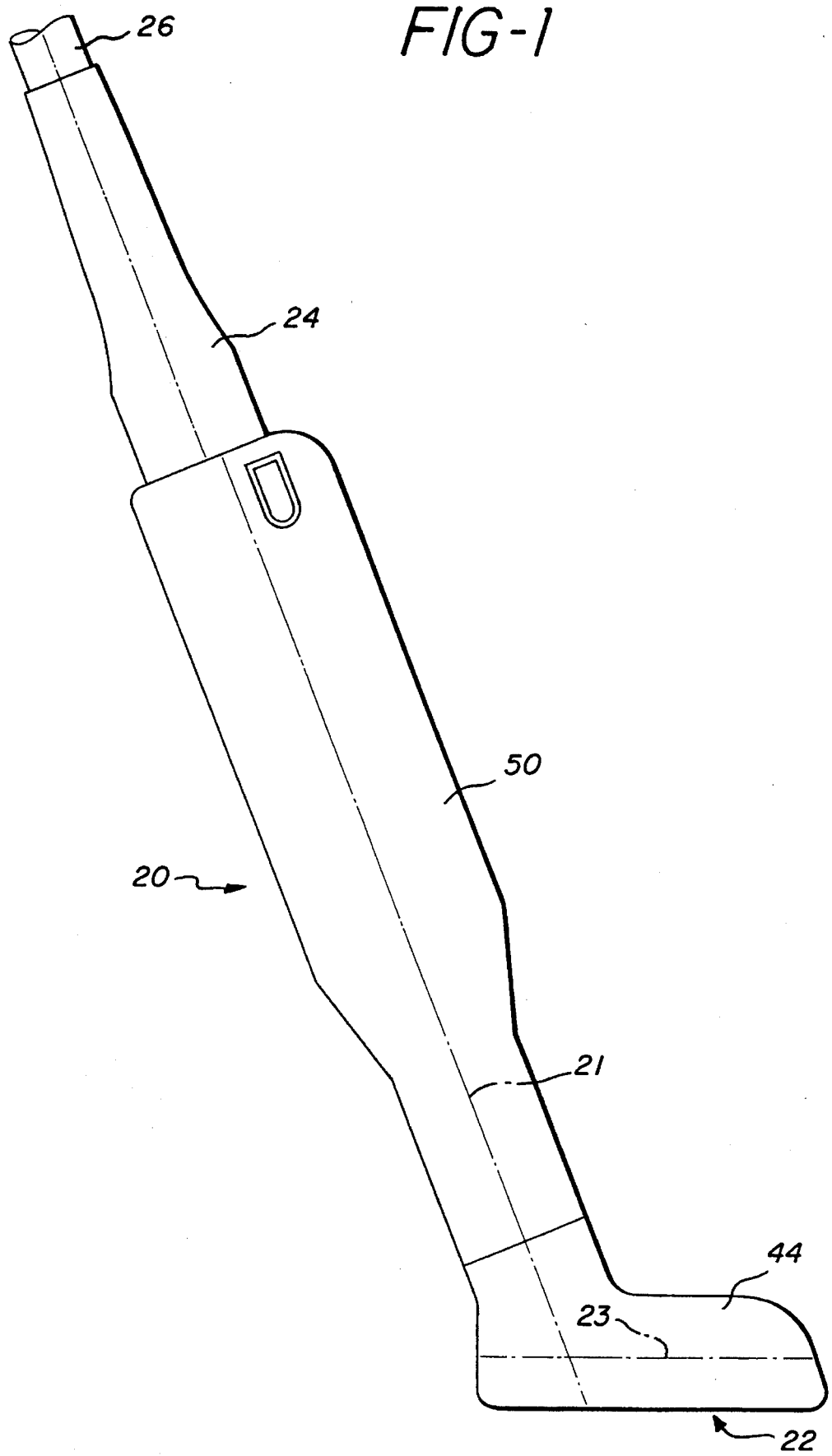
FIG. 1 illustrates the outline of an intraoperative ultrasound probe of the present invention.
Figure 2:
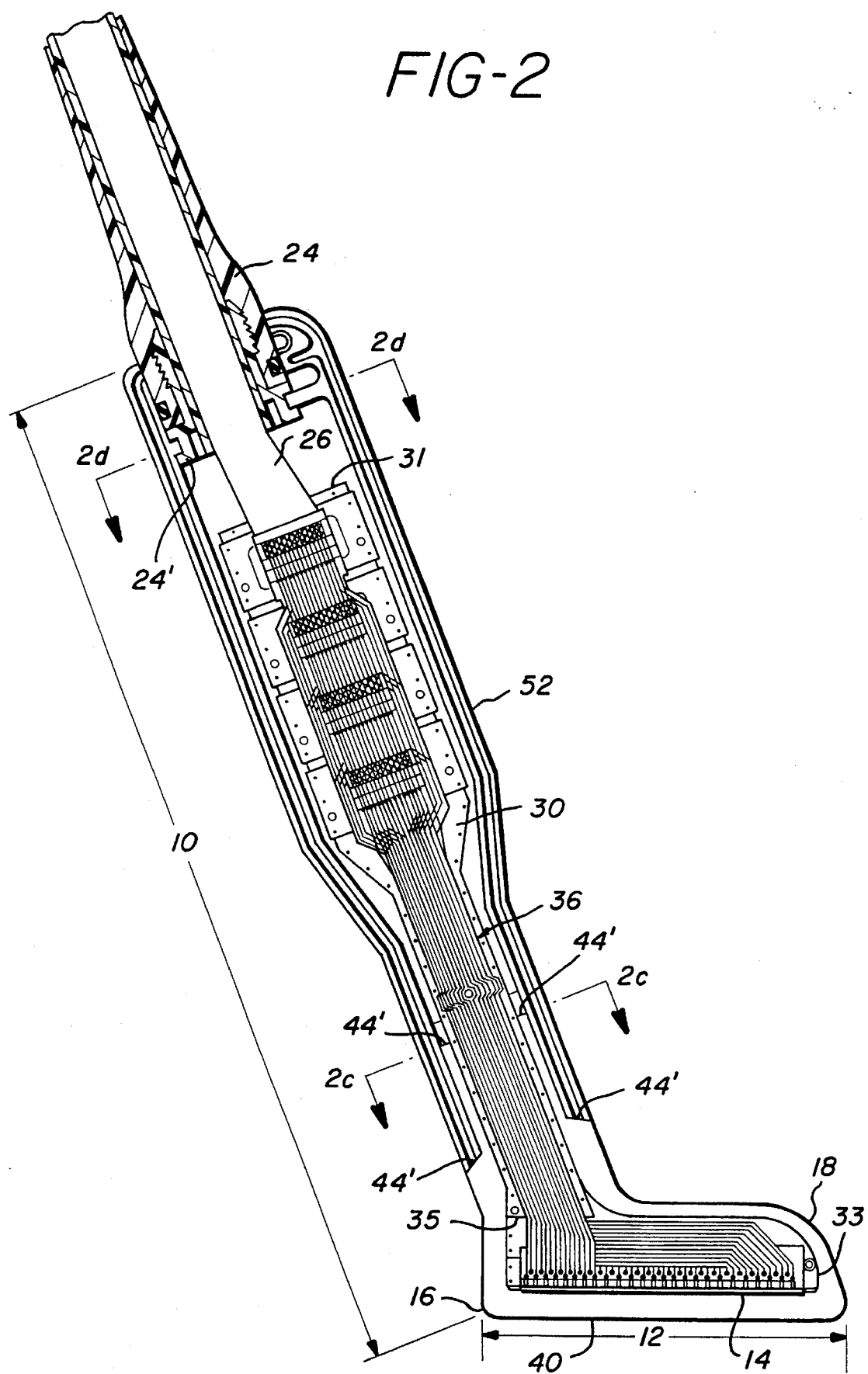
FIG. 2 illustrates a side view of the interior of the intraoperative ultrasound probe of FIG. 1.

Referring first to FIGS. 1 and 2, an intraoperative ultrasound probe constructed in accordance with the principles of the present invention and specifically designed for vascular surgical applications is shown. The probe is approximately L-shaped, resembling a tiny model of a leg and foot. The probe comprises a distal transducer section 22 resembling a boot on the "foot" and a handle section 20 resembling the "leg" with a strain relief 24 and multifilament cable 26 exiting the proximal end of the handle section 20. The cable leads to a connector (not shown) suitable for connecting the probe to an ultrasonic diagnostic system which drives the transducer of the probe and receives ultrasonic echo signals from the transducer in the conventional manner. A case with halves 50 and 52 form the exterior of the handle section 20 and the transducer section boot 44 is formed of molded rubber. The major axis 23 of the transducer section 22 is inclined at an angle of 112° with respect to the major axis 21 of the handle section. The length 10 of the handle section 20 from its proximal end to the heel 16 of the transducer section 22 is approximately 95 mm. The length 12 of the transducer section from heel 16 to its toe 18 is approximately 34.5 mm and the width 28 of the transducer section (FIG. 2a) is approximately 12 mm.

Figure 2A:
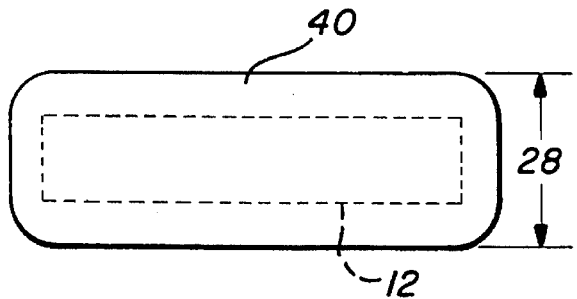
FIGS. 2a–2d illustrate various bottom, end and cross-sectional views of the probe of FIG. 2.
Figure 2B:
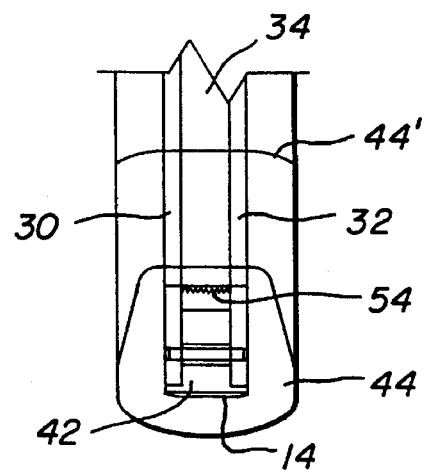
Figure 2C:
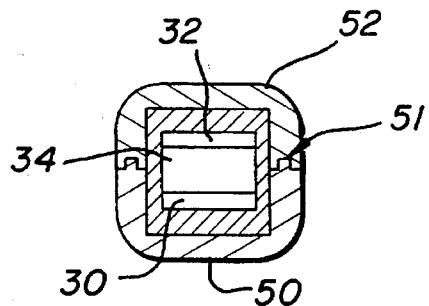
Figure 2D:
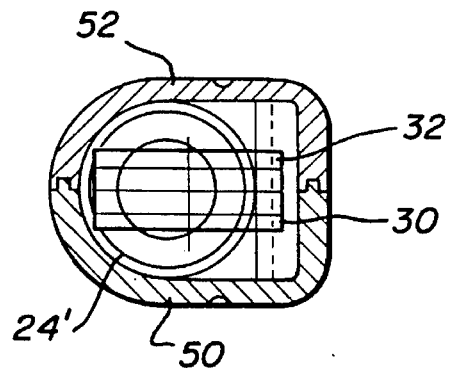

Referring now to FIGS. 2 and 2a–2d, two matched printed circuit boards 30 and 32 are located inside the case 50, 52 and boot 44, each board having the inclined L-shape of the probe. Each printed circuit board extends from a top end 31 to a bottom distal end 33. The printed circuit boards are mounted in parallel, separated as shown in FIGS. 2b–2d by an insulating spacer 34, extending from the top 31 of the printed circuit boards to a lower terminating edge 35. Each printed circuit board contains a plurality of conductive traces 36, which make electrical connections between the transducer crystal 14 and the upper surfaces of the boards where connections are made to wires 38 of the multifilament cable 26.

The transducer crystal 14 is mounted perpendicular to the lower edges of the printed circuit boards 30 and 32 as shown in FIGS. 2, 2a, and 2b. The crystal 14 has an overall length of approximately 27 mm and a width of approximately 4.6 mm. The crystal 14 is diced into an array of 128 finely pitched elements for the performance of B-scan and color flow Doppler imaging. The finely pitched elements transmit and receive over an operating frequency range of 5–10 MHz, giving the transducer the ability to visualize and diagnose a vessel which is immediately in contact with the footprint 40 of the probe. The footprint of the probe is shown in the bottom view of FIG. 2a, with the outline 14' of the transducer crystal indicated by a dashed line box.

The transducer crystal 14 is plated on its upper and lower surfaces with layers of conductive foil, one of which is cut by the dicing process. A plurality of metallic TAB leads are bonded at one end to the diced conductive foil with the other end of each TAB lead being bonded to a conductive trace 36 at the edges of the printed circuit boards 30 and 32. TAB lead connections as described in U.S. patent application Ser. No.

07/929,736, filed Aug. 13, 1992, are made to both the ground (undiced) and signal (diced) side of each piezoelectric element of the crystal and thence to the printed circuit boards 30 and 32.

Figure 3:
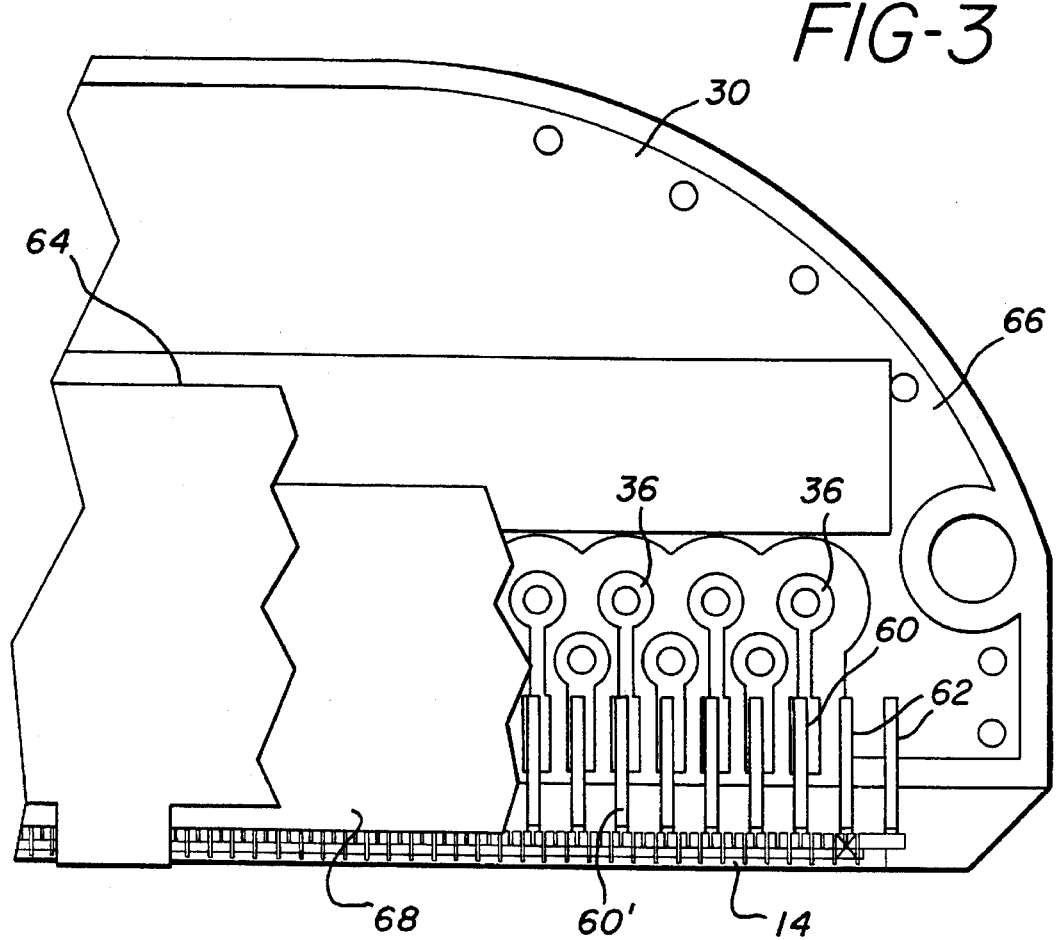
FIG. 3 is a partially cutaway view of the distal end of the probe of FIG. 2.

Turning to FIG. 3, the manner in which electrical connections are made between the elements of the transducer crystal 14 and the conductive traces 36 of the printed circuit boards 30 and 32 is shown in enlarged detail. TAB leads 60, 60' are soldered at one end to the conductive foil strips on the inner surface of the transducer crystal 14. These strips have been formed, as mentioned above, by the dicing process. Two TAB leads 62 are connected to foil strips of inactive elements at the end of the transducer array. The other ends of the TAB leads 60 and 60' are soldered to conductive traces 36 on the printed circuit board 30. The ends of TAB leads 62 are soldered to the ground plane 66 of the printed circuit board.

A ground foil 64 folds over the outer foil surface of the transducer crystal and is attached to that foil surface to ground it. The ground foil 64 is also electrically connected to the ground plane 66 of the printed circuit board. A sheet 68 of nonconductive material insulates the conductive traces 36 from the ground foil 64.

It will also be noted in FIG. 3 that TAB leads are only connected to alternating transducer elements. In this preferred embodiment, electrical connection is made to odd numbered elements from printed circuit board 32, and to even numbered elements from printed circuit board 30.

Returning to FIG. 2 and 2a–2e, the volume 42 behind the transducer crystal and below the terminating edge 35 of the spacer 34, and between the printed circuit boards, is filled with a loaded epoxy backing material to a depth as indicated by the jagged upper surface 54 of the backing material in FIG. 2b. The backing material attenuates acoustic waves emanating from the rear of the crystal. The entire transducer section is then encased in an RTV rubber compound by a molding process which forms the boot 44. As FIGS. 2 and 2b show, the RTV rubber casing 44 is approximately 2.5 mm thick below the transducer 14. This gives the probe an inherent standoff distance between the crystal and the vascular structure of the body that is in contact with the footprint 40 of the probe. The standoff distance allows vessels in contact with the footprint to be clearly imaged, as the standoff distance enables the return of ultrasonic echoes from the contacted vessel to return to a plurality of transducer elements for focusing in flow and image processing.

The RTV rubber casing 44 extends to edges 44' along the handle section of the probe and inside the case halves 50 and 52. If desired, the molding process can also form an integral liquid tight gasket 45 in the rubber where the lower portion of the case closes around the boot (see FIG. 5). The encapsulating boot thus completely seals the transducer end of the probe, fully insulating the patient from the electrical connections to the transducer crystal. The encapsulating boot also renders the probe easy to clean and sterilize between uses, further enhancing patient safety and medical efficiency.

The handle section 20 above the edges 44' of the RTV rubber casing 44 comprises two hollow clamshell case halves 50 and 52 formed of a rigid polysulfone plastic. The case 50, 52 encloses the upper extension of the printed circuit boards 30 and 32 where connections are made to to the wires 38 of the cable 26. One technique for attaching the wires 38 of the cable 26 to the printed circuit boards 30 and 32 is shown in FIG. 4, 5, and 6.

The preferred cable is comprised of 128 individual coaxial conductors. In FIG. 4 reference numeral 38 designates the outer sheaths of several of these coaxial conductors. The outer sheaths terminate to expose the braided ground shields 72 of the coax, and these ground shields are soldered to a grounding pad 76 on the printed circuit board. The ground shields terminate and following a short length of inside insulating sheath the center conductors 74 of the coax are exposed. These center conductors are soldered to individual conductive signal traces 36 on the printed circuit board.

As FIG. 5 shows, the coax wires are connected to the boards in groups of sixteen as denoted by terminating assemblies 80, 182, 184, and 186. Each terminating assembly terminates at a different distance along the cable so that the wires of each terminating assembly overlay the previous assemblies when attached to their positions on the printed circuit boards. This overlap is shown in FIG. 6. In correspondence with the electrical connections to the transducer elements, odd numbered wires are connected to one of the printed circuit boards, and even numbered wires are connected to the other board. For ease of illustration of the termination assemblies, the overlapping wires have not been shown in FIG. 5 but are illustrated in the profile view of FIG. 6.

Figure 7E:
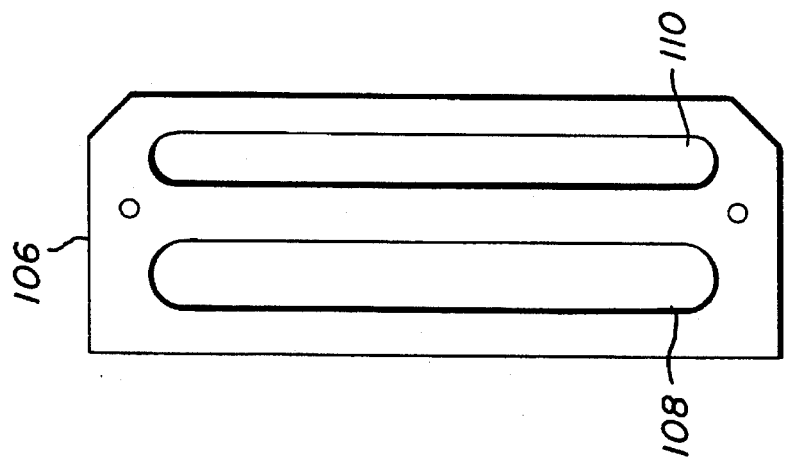
Figure 7D:
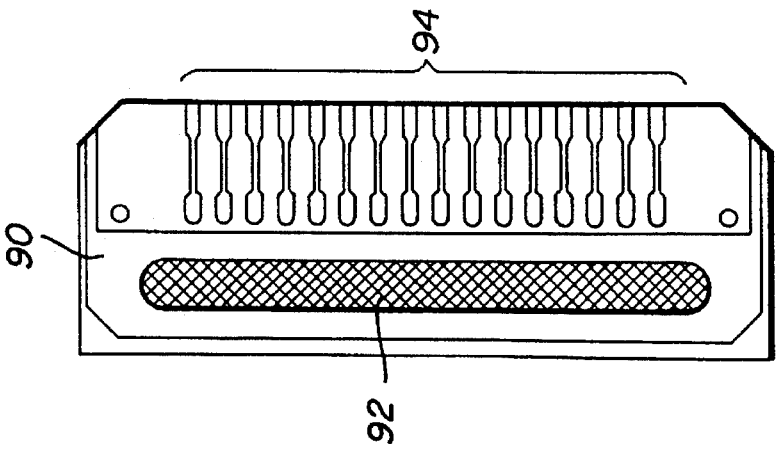

Preferably the cables are preassembled with the conductors of the coaxial wires soldered to terminating assemblies. The terminating assemblies are then easily soldered in position on the printed circuit boards 30 and 32. A preferred terminating assembly is shown in FIGS. 7a–7e and 8. Each terminating assembly is a multilayered panel of copper foil patterns and insulating sheets made of a flexible, insulating polyimide material. The terminating assembly includes a center polyimide sheet 82 as shown in FIG. 7c. Photoetched on one side of the center sheet 82 is a line 96 of sixteen foil pads. Photoetched on the other side of the center sheet is a ground plane 90 with a central screen-like foil pattern 92, and sixteen bridging lines 94. Electrical through hole connections known as vias connect each pad 96 to a bridging line 94 on the other side of the center sheet 82. Apertures 84 and 86 are then formed in the center sheet 82, resulting in bridging lines 94 bridging the aperture 86 and the screen-like pattern 92 extending across aperture 84.

The assembly is completed by laminating an upper polyimide sheet 100 to the top of the center sheet, with aperture 102 exposing pads 96 and bridging lines 94, and aperture 104 exposing the copper screen 92. A lower polyimide sheet 106 with aligning apertures is laminated to the other side of the center sheet.

Each terminating assembly is attached to sixteen coaxial wires of the cable 26 as shown in FIG. 8. The braided ground shields 72 are soldered to the screen-like foil pattern 92. During this process it is intended that solder will flow through the holes in the screen to the back side of the screen. The center coaxial conductors 74 are soldered to the individual foil pads 96 through aperture 102. Electrical connection is formed from the conductors 74 to the bridging lines 94 through the interconnecting vias.

Attachment of the cable to printed circuit boards 30 and 32 is now quick and easy. The screen-like foil pattern is positioned over the grounding pad 76 on the printed circuit board with the bridging lines 94 aligned with their mating conductive traces 36 on the board. In one operation the solder which flowed through to the back of the screen 92 is heated to attach the ground shields and screen to the pad 76. If an insufficient amount of solder flowed to the back side of the screen during the prior assembly step, this soldering step may be augmented by providing additional solder to the ground shields so that the shields and screen a securely soldered to the pad 76. A second operation simultaneously contacts bridging lines 94 through aperture 102 and solders the lines 94 to the underlying conductive traces 36. The soldering of the bridging lines should not loosen the conductors 74 from pads 96 due to the low thermal conductivity of the electrically interconnecting vias. In this manner the eight terminating assemblies 80, 80', 182–196 and 182'–186' are quickly attached to the printed circuit boards of the probe.

After all of these electrical connections have been made, the case 50, 52 is closed around the RTV rubber casing 44 at the distal end of the case and a flange 24' of the strain relief 24 at the proximal end of the case and sealed with an RTV adhesive to form a liquidtight enclosure, thereby enabling the probe to be safely and reliably used in a surgical field and thereafter sterilized.

As FIGS. 2c and 2d show, at the wider top of the handle the case is rounded in the back with squared corners in the front (FIG. 2d), and makes a transition to its narrower, lower dimension where it is approximately square in cross-section (FIG. 2c). This shape enables the surgeon to hold and handle the probe in the manner of a surgical instrument, with the rounded back resting between the thumb and forefinger and the squared corners affording a secure grip for the fingers.

The inclined L-shape of the probe enables the surgeon to grasp the handle section 20 and manipulate the probe without the hand obscuring the surgical site and vessel being contacted by the probe footprint 40. The transducer section 22 can be moved along a vessel to image the vessel even beyond the extent of an incision, because the toe 18 of the transducer section can be inserted under the skin at the end of the incision. This enables the surgeon to view and diagnose flow conditions in the vessel beyond the incision site.

What is claimed is:

1. A termination assembly for retaining coaxial wires of a multiwire cable in a predetermined alignment for attachment of said coaxial wires to conductive traces of a printed circuit comprising:

a planar body having an aperture located therein;

a plurality of said coaxial wires attached to said planar body and traversing said aperture in said predetermined alignment, the electrical paths of the central conductors of said coaxial wires being simultaneously accessible through said aperture to electrically connect said central conductors to aligned conductive traces of a printed circuit; and wherein the electrical paths of the shield conductors of said coaxial wires are accessible through said aperture to electrically connect said shield conductors to a ground plane of said printed circuit.

2. The termination assembly of claim 1, wherein said planar body comprises first and second sheets of nonconductive material each having aligning first and second apertures, wherein electrical paths of said plurality of coaxial wires are located intermediate said first and second sheets, and wherein the electrical paths of the central conductors of said coaxial wires traverse said aligned first apertures, and wherein the electrical paths of the shield conductors of said coaxial wires traverse said aligned second apertures.

3. The termination assembly of claim 2, further comprising a plurality of conductive pads aligned with said electrical paths of the central conductors, wherein said conductive pads are suitable for connection to individual ones of the central conductors of said coaxial wires.

4. A termination assembly for attaching coaxial wires of a multiwire cable to conductive traces of a printed circuit comprising:

a flexible planar body having first and second apertures located therein;

a plurality of conductive lines traversing said first aperture and suitable for connection to individual ones of the central conductors of said coaxial wires and to conductive traces of a printed circuit board; and a sheet of conductive material traversing said second aperture and suitable for common connection to the shield conductors of said coaxial wires and to a ground plane of said printed circuit board with said shield conductors and said ground plane both aligned with said second aperture, wherein said flexible planar body comprises first and second sheets of nonconductive material each having aligning first and second apertures, wherein said conductive lines and material are located intermediate said first and second sheets, and wherein said conductive lines traverse said aligned first apertures, and wherein said sheet of conductive material traverses said aligned second apertures; and further comprising a third sheet of nonconductive material having first and second apertures aligning with the first and second apertures of said first and second sheets, wherein said conductive lines and conductive material are affixed to said third sheet, and wherein said third sheet is laminated between said first and second sheets.

5. A termination assembly for retaining coaxial wires of a multiwire cable in a predetermined alignment for attachment of said coaxial wires to conductive traces of a printed circuit comprising:

a flexible planar body having an elongated aperture located therein; and a plurality of coaxial wires of said multiwire cable attached to said planar body with portions of said coaxial wires aligned substantially in parallel and bridging said elongated aperture, with the central conductor electrical paths of said plurality of coaxial wires exposed over a portion of said bridging portion of said coaxial wires and the shield conductor electrical paths of said plurality of coaxial wires exposed over a portion of said bridging portion of said coaxial wires, wherein said exposed portions of said central conductor electrical paths are simultaneously accessible through said aperture to electrically connect said central conductors of said coaxial wires to conductive traces of a printed circuit, and said exposed portions of said shield conductor electrical paths are simultaneously accessible through said aperture to electrically connect said shield conductors of said coaxial wires to a conductive trace of a printed circuit.

6. The termination assembly of claim 5, further comprising means for aligning said planar body and said plurality of attached coaxial wires with said printed circuit so that said central conductor electrical paths are respectively aligned with the conductive traces of said printed circuit to which they are to be electrically connected.

7. The termination assembly of claim 5, further comprising first and second holes located on opposite ends of said planar body.

8. A termination assembly for retaining coaxial wires of a multiwire cable in a predetermined alignment for attachment of said coaxial wires to conductive traces of a printed circuit comprising:

a flexible planar body comprising first and second sheets of nonconductive material each having aligning first and second apertures; and a plurality of coaxial wires of said multiwire cable attached to said planar body with portions of said coaxial wires aligned substantially in parallel and electrically bridging said aligned first and second apertures, with the central conductor electrical paths of said plurality of coaxial wires exposed over portions of said central conductor electrical paths which bridge said first apertures, and the shield conductor electrical paths of said plurality of coaxial wires exposed over portions of said coaxial wires which bridge said second apertures, wherein said exposed portions of said central conductor electrical paths are simultaneously accessible through said first apertures to electrically connect said central conductors of said coaxial wires to conductive traces of a printed circuit, and said exposed portions of said shield conductor electrical paths are simultaneously accessible through said second apertures to electrically connect said shield conductors of said coaxial wires to a conductive trace of a printed circuit.

9. The termination assembly of claim 8, further comprising a sheet of conductive material traversing said second aperture and suitable for common connection to the shield conductors of said coaxial wires and to a ground plane of said printed circuit, wherein said sheet of conductive material further comprises a plurality of perforations permitting the flow of solder therethrough.

10. The termination assembly of claim 8, further comprising means for aligning said planar body and said plurality of attached coaxial wires with said printed circuit so that said central conductor electrical paths are respectively aligned with the conductive traces of said printed circuit to which they are to be electrically connected.

11. The termination assembly of claim 8, further comprising first and second holes located on opposite ends of said planar body.

* * * * *

UNITED STATES PATENT AND TRADEMARK OFFICE
CERTIFICATE OF CORRECTION

PATENT NO. : 5,482,047
DATED : January 9, 1996
INVENTOR(S) : Timothy F. Nordgren et al.

It is certified that error appears in the above-indentified patent and that said Letters Patent is hereby corrected as shown below:

On the title page: Item [75]
    Inventors: "Timothy F. Nordgren, Bothell Washington; Deborah K. Imling, Bellevue Washington; Joseph L. Ungari, Everett Washington; Donald G. Killam, Woodinville Washington; Ronald E. McKeighen, Woodinville Washington" should be --Timothy F. Nordgren, Bothell Washington; Donald G. Killam, Woodinville Washington--

Signed and Sealed this

Twenty-eighth Day of May, 1996

Attest:

BRUCE LEHMAN

Attesting Officer     Commissioner of Patents and Trademarks